United States Patent [19]

Heinemann et al.

[11] Patent Number: 5,416,088
[45] Date of Patent: May 16, 1995

[54] SUBSTITUTED PYRIDYLPYRIMIDINES, THEIR PREPARATION AND THEIR USE

[75] Inventors: Ulrich Heinemann, Leichlingen; Heinz-Wilhelm Dehne, Monheim; Stefan Dutzmann, Hilden; Christoph Erdelen, Leichlingen, all of Germany

[73] Assignee: Bayer Aktiengesellschaft, Leverkusen, Germany

[21] Appl. No.: 107,670

[22] PCT Filed: Feb. 13, 1992

[86] PCT No.: PCT/EP92/00311

§ 371 Date: Aug. 16, 1993

§ 102(e) Date: Aug. 16, 1993

[87] PCT Pub. No.: WO92/14726

PCT Pub. Date: Sep. 3, 1992

[30] Foreign Application Priority Data

Feb. 23, 1991 [DE] Germany .................. 41 05 751.1

[51] Int. Cl.⁶ .................. C07D 401/04; A01N 43/54
[52] U.S. Cl. ..................... 514/256; 544/333
[58] Field of Search ............... 514/256; 544/333

[56] References Cited

FOREIGN PATENT DOCUMENTS 270362 6/1988 European Pat. Off. .
322391 6/1989 European Pat. Off. .
WO91/07400 5/1991 WIPO .

Primary Examiner—John M. Ford
Attorney, Agent, or Firm—Sprung Horn Kramer & Woods

[57] ABSTRACT

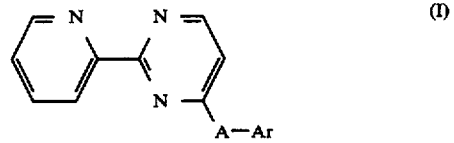

Substituted pyridylpyrimidines have formula (I), in which A and Ar have the meaning given in the test of the description. Also disclosed are their preparation, their use and new initial products. The compounds having formula (I) may be prepared from appropriate salts of 2-pyridylamidine with appropriate enamines; said enamines are also new and disclosed by the invention, and may be prepared from appropriate ketones with appropriate formaldehyde derivates.

5 Claims, No Drawings

SUBSTITUTED PYRIDYLPYRIMIDINES, THEIR PREPARATION AND THEIR USE

This application is a 371 of PCT/EP92/00311filed Feb 13, 1992.

The invention relates to novel substituted pyridylpyrimidines, to a process for their preparation, to their use as pesticides, and to novel intermediates.

It has been disclosed that certain substituted pyridylpyrimidines such as, for example, the compound 2-(6-phenyl-2-pyridyl)-4-chloro-6-methylpyrimidine or the compound 2-(6-methyl-2-pyridyl)-4-(2-methylphenyl)-pyrimidine or the compound 2-(6-methyl-2-pyridyl)-4-hydroxy-6-phenylpyrimidine have fungicidal properties (cf., for example, EP 259,139 or EP 270,362). However, the activity of these previously known compounds is not entirely satisfactory in all fields of application, in particular when low amounts and concentrations are applied.

Novel substituted pyridylpyrimidines of the general formula ( I )

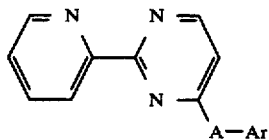

in which
A represents a radical of the formula

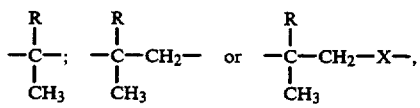

where
R in each case represents alkyl,
X represents oxygen or sulphur and
Ar represents optionally substituted phenyl, have been found.

Furthermore, it has been found that the novel substituted pyridylpyrimidines of the general formula (I),

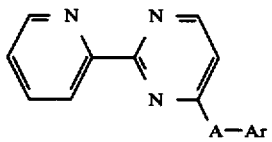

in which
A represents a radical of the formula

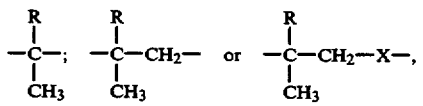

where
R in each case represents alkyl,
X represents oxygen or sulphur and
Ar represents optionally substituted phenyl, are obtained when 2-pyridylamidine salts of the formula (II)

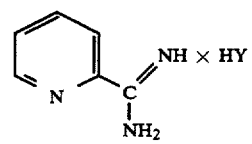

in which
Y represents the anion of an inorganic mineral acid, are reacted with enamines of the formula (III)

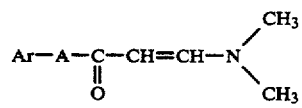

in which
Ar and A have the abovementioned meaning, if appropriate in the presence of a diluent and if appropriate in the presence of a reaction auxiliary.

Finally, it has been found that the novel substituted pyridylpyrimidines of the general formula (I) have a good activity against pests.

Surprisingly, the substituted pyridylpyrimidines of the general formula (I) according to the invention show a markedly improved activity, for example against phytopathogenic fungi, when compared with the substituted pyridylpyrimidines which are known from the prior art, for example the compound 2-(6-phenyl-2-pyridyl)-4-chloro-6-methylpyrimidine or the compound 2-(6-methyl-2-pyridyl)-4-(2-methylphenyl)-pyrimidine or the compound 2-(6-methyl-2-pyridyl)-4-hydroxy-6-phenyl-pyrimidine, which are similar compounds chemically and from the point of view of their action.

Formula (I) provides a general definition of the substituted pyridylpyrimidines according to the invention.

Preferred compounds of the formula (I) are those in which
A represents a radical of the formula

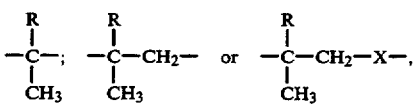

where
R in each case represents straight-chain or branched alkyl having 1 to 4 carbon atoms,
X represents oxygen or sulphur and
Ar represents phenyl which is optionally monosubstituted to pentasubstituted by identical or different substituents, suitable substituents being: halogen, cyano, nitro, in each case straight-chain or branched alkyl, alkoxy or alkylthio, in each case having 1 to 4 carbon atoms, in each case straight-chain or branched halogenoalkyl, halogenoalkoxy or halogenoalkylthio, in each case having 1 to 4 carbon atoms and 1 to 9 identical or different halogen atoms, in each case straight-chain or branched alkoxycarbonyl or alkoxyiminoalkyl, in each case having 1 to 4 carbon atoms in the individual alkyl moieties, or phenyl which is optionally monosubstituted to pentasubstituted by identical or different substituents from the series comprising halogen and/or straight-chain or branched alkyl having 1 to 4 carbon atoms.

Particularly preferred compounds of the formula (I) are those in which

A represents a radical of the formula

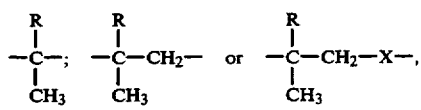

where

R in each case represents methyl or ethyl,

X represents oxygen or sulphur and

Ar represents phenyl which is optionally monosubstituted to trisubstituted by identical or different substituents, suitable substituents being: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, trifluoromethylthio, methoxycarbonyl, ethoxycarbonyl, methoxyiminomethyl, ethoxyiminomethyl, methoxyiminoethyl, ethoxyiminoethyl, or phenyl which is optionally monosubstituted to trisubstituted by identical or different substituents from the series comprising fluorine, chlorine, bromine, methyl and/or ethyl.

Very particularly preferred compounds of the formula (I) are those in which

A represents a radical of the formula

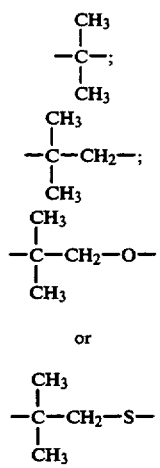

and

Ar represents phenyl which is optionally monosubstituted or disubstituted by identical or different substituents, suitable substituents being: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, trifluoromethylthio, methoxycarbonyl or ethoxycarbonyl.

In addition to the compounds mentioned in the Preparation Examples, the following substituted pyridylpyrimidines of the general formula (I) may be mentioned individually:

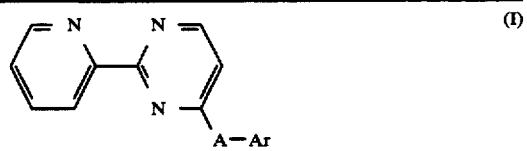

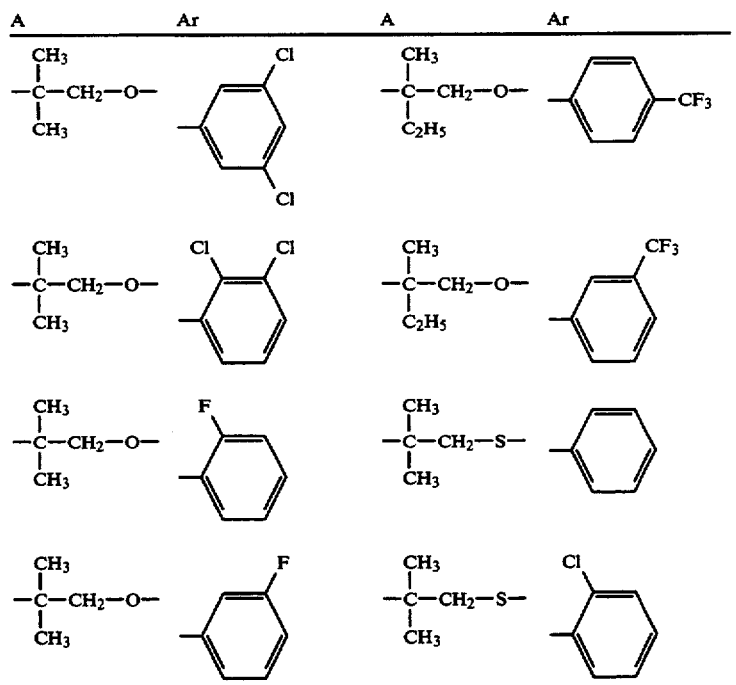

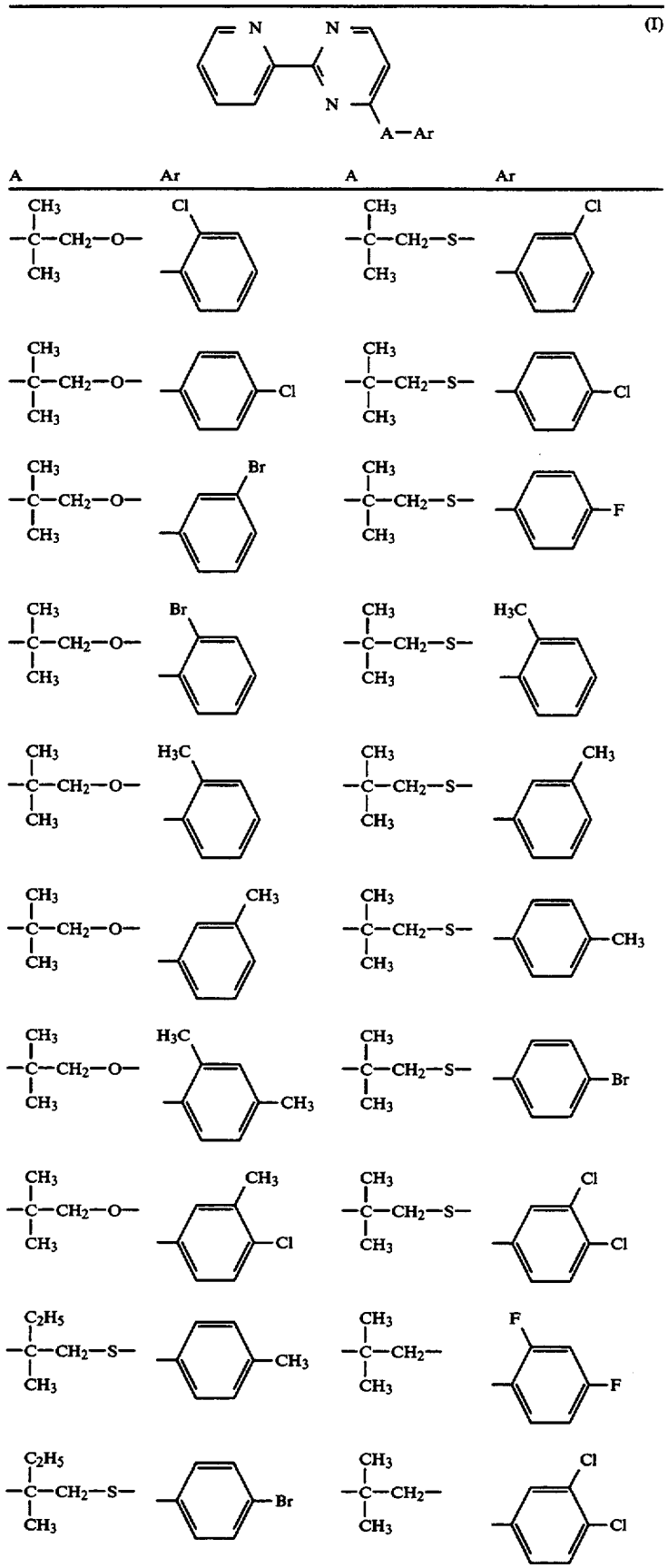

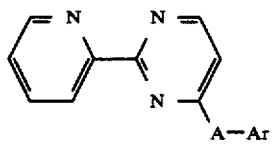

| A | Ar | A | Ar |
|---|---|---|---|
| -C(CH₃)₂-CH₂- | 3,5-dichlorophenyl | -C(C₂H₅)(CH₃)-CH₂- | phenyl |
| -C(CH₃)₂-CH₂- | 2,3-dichlorophenyl | -C(C₂H₅)(CH₃)-CH₂- | 4-Cl-phenyl |
| -C(CH₃)₂-CH₂- | 4-CF₃-phenyl | -C(C₂H₅)(CH₃)-CH₂- | 3-Cl-phenyl |
| -C(CH₃)₂-CH₂- | 3-CF₃-phenyl | -C(C₂H₅)(CH₃)-CH₂- | 2-Cl-phenyl |
| -C(CH₃)₂-CH₂- | 2-CF₃-phenyl | -C(C₂H₅)(CH₃)-CH₂- | 4-F-phenyl |
| -C(CH₃)₂-CH₂- | 4-OCH₃-phenyl | -C(C₂H₅)(CH₃)-CH₂- | 4-CH₃-phenyl |
| -C(CH₃)₂-CH₂- | 3-OCH₃-phenyl | -C(CH₃)₂- | 4-Cl-phenyl |
| -C(CH₃)₂-CH₂- | 2-OCH₃-phenyl | -C(CH₃)₂- | 4-Br-phenyl |
| -C(CH₃)₂-CH₂- | 3-F-phenyl | -C(CH₃)₂- | 4-F-phenyl |
| -C(CH₃)₂-CH₂- | 4-Br-phenyl | -C(CH₃)₂- | 4-CH₃-phenyl |

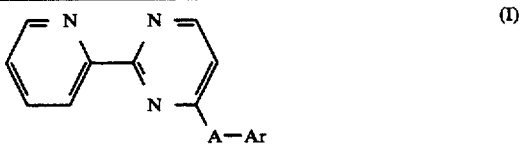

| A | Ar | A | Ar |
|---|---|---|---|
| CH3-C(CH3)-CH2- | 3-Br-phenyl | -C(CH3)2- | 3-CH3-phenyl |
| CH3-C(CH3)-CH2- | 2,3-diCH3-phenyl | -C(CH3)2- | 2-CH3-phenyl |
| -C(CH3)2- | 2,4-diCl-phenyl | -C(CH3)2- | 2-Cl-phenyl |
| -C(CH3)2- | phenyl | -C(CH3)2- | 3,4-diCl-phenyl |
| -C(CH3)2- | 4-Cl-phenyl | -C(CH3)2- | 2,4-diF-phenyl |
| -C(CH3)2- | 2-Cl-phenyl | | |

If, for example, 2-pyridylamine hydrochloride and 1-dimethylamino-4,4-dimethyl-5-(4methylphenyl)-pent-1-en-3-one are used as starting compounds, the course of the reaction of the process according to the invention can be represented by the following equation:

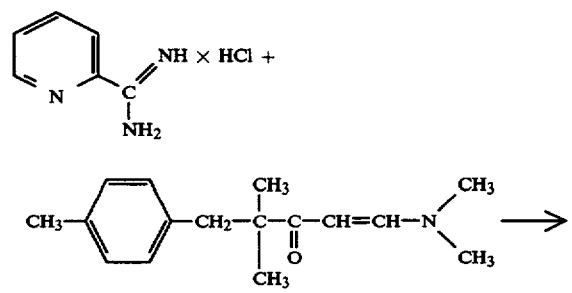

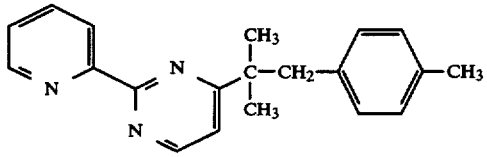

Formulation (II) provides a general definition of the 2-pyridylamidine salts required as starting substances for carrying out the process according to the invention. In this formula (II), Y preferably represents a halide anion or a hydrogen sulphate anion, in particular a chloride anion, a bromide anion or a hydrogen sulphate anion. Y particularly preferably represents a chloride anion.

The 2-pyridylamidine salts of the formula (II) are known (cf., for example, U.S. Pat. No. 4,018,770 or J. Am. Chem. Soc. 107, 5745–5754 [1985] or J. Med. Chem. 33, 1230–1241 [1990]).

Formula (III) provides a general definition of the enamines furthermore required as starting substances for carrying out the process according to the invention. In this formula (III), Ar and A preferably represent those radicals which have already been mentioned in connection with the description of the substances of the formula (I) according to the invention as being preferred for these substituents.

The enamines of the formula (III) were hitherto unknown and are also a subject of the invention.

They are obtained when ketones of the formula (IV).

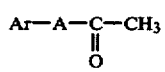  (IV)

in which
Ar and A have the abovementioned meaning, are reacted with formaldehyde derivatives of the formula (V),

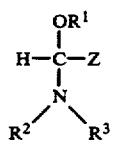  (V)

in which
Z represents a radical —O—R¹ or a radical

and
R¹, R² and R³ independently of one another in each case represent alkyl, in particular straight-chain or branched alkyl having 1 to 4 carbon atoms,
in approximately equimolar amounts, if appropriate in the presence of a dipolar aprotic diluent such as, for example, dimethylformamide, N-methylformanilide, N-methylpyrrolidone, dioxane, ethylene glycol dimethyl ether, ethylene glycol diethyl ether or hexamethylphosphoric triamide, but preferably without the addition of a diluent, at temperatures between 20° C. and 160° C., preferably between 100° C. and 140° C.

Ketones of the formula (IV) are known or can be obtained in analogy to known processes (cf., for example, U.S. Pat. No. 4,877,446; EP 301,393; EP 296,749; EP 289,913; DE 3,643,851; GB 2,120,664; DE 3,210,725; DE 3,021,516).

Formaldehyde derivatives of the formula (V) are generally known compounds of organic chemistry.

The abovementioned definitions of the individual radicals of the formula (I) also apply analogously to the intermediates and precursors.

Suitable diluents for carrying out the process according to the invention are inert organic solvents. These include, in particular, aliphatic, alicyclic or aromatic, optionally halogenated hydrocarbons such as, for example, benzine, benzene, toluene, xylene, chlorobenzene, petroleum ether, hexane, cyclohexane, dichloromethane, chloroform, carbon tetrachloride, ethers such as diethyl ether, dioxane, tetrahydrofuran or ethylene glycol dimethyl ether or ethylene glycol diethyl ether, ketones such as acetone or butanone, nitriles such as acetonitrile or propionitrile, amides such as dimethylformamide, dimethylacetamide, N-methylformanilide, N-methylpyrrolidone or hexamethylphosphoric triamide, esters such as ethyl acetate, sulphoxides such as dimethyl sulphoxide, or alcohols such as methanol, ethanol and also n- or i-propanol.

The process according to the invention is preferably carried out in the presence of a suitable reaction auxiliary. Suitable reaction auxiliaries are all inorganic or organic bases which can be customarily be used. The following are preferably used: the hydrides, hydroxides, amides, alcoholates, carbonates or hydrogen carbonates of alkali metals, such as, for example, sodium hydride, sodium amide, sodium hydroxide, sodium methylate, sodium ethylate, potassium t-butylate, sodium carbonate or sodium hydrogen carbonate, and also tertiary amines such as, for example, triethylamine, N,N-dimethylaniline, pyridine, N,N-dimethylaminopyridine, diazabicyclooctane (DABCO), diazabicyclononene (DBN) or diazabicycloundecene (DBU).

When carrying out the process according to the invention, the reaction temperatures can be varied within a substantial range. In general, the process is carried out at temperatures between 20° C. and 140° C., preferably at temperatures between 60° C. and 120C.

In general, the process according to the invention is carried out under atmospheric pressure. However, it is also possible to carry out the process according to the invention under increased or reduced pressure.

To carry out the process according to the invention, 0.8 to 1.5 moles, preferably 1.0 to 1.2 moles, of an enamine of the formula (III) and, if appropriate, 1.0 to 2.0 moles, preferably 1.0 to 1.5 moles, of reaction auxiliary are generally employed per mole of 2-pyridylamidine salt of the formula (II).

The reaction is carried out and the reaction products are worked up and isolated by generally customary methods (cf. also the Preparation Examples).

The active compounds according to the invention have a powerful action against pests and can be employed in practice for combating undesired harmful organisms. The active compounds are particularly suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum*; Phytophthora species, such as, for example, *Phytophthora infestans*;

Pseudoperonospora species, such as, for example, *Pseudoperonospora humuli* or *Pseudoperonospora cubensis*;

Plasmopara species, such as, for example, *Plasmopara viticola*;

Peronospora species, such as, for example, *Peronospora pisi* or *P. brassicae*;

Erysiphe species, such as, for example, *Erysiphe graminis*;

Sphaerotheca species, such as, for example, *Sphaerotheca fuliginea*;

Podosphaera species, such as, for example, *Podosphaera leucotricha*;

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus satius* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocerosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success for combating cereal diseases such as, for example, against the pathogen causing powdery cereal mildew on wheat or barley (*Erysiphe graminis*) or against the pathogen causing leaf spot on barley (*Cochliobolus sativus*) or against the pathogen causing leaf spot on wheat (*Leptosphaeria nodorum*) or against the pathogen causing net blotch on barley (*Pyrenophora teres*) or against the pathogen causing snow blight on cereals (*Fusarium nivale*) and against other Fusarium pathogens such as, for example, *Fusarium culmorum*, moreover for combating diseases in rice growing such as, for example, against the pathogen causing rice blast disease (*Pyricularia oryzae*) or against the pathogen causing rice stem blight (*Pellicularia sasakii*) or for combating diseases in viticulture such as, for example, against the pathogen causing mildew on grape vines (*Uncinula necator*).

In addition, mention must be made of a broad in-vitro action.

Besides, the active compounds are suitable for combating animal pests, preferably arthropods and nematodes, in particular insects and arachnida which are encountered in agriculture, in forests, in the protection of stored products and of materials, and in the hygiene field, and have good plant tolerance and favourable toxicity to warm-blooded animals. They are active against normally sensitive and resistant species and against all or some stages of development. The above-mentioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella mmaculata.* From the order of the Thysanura, for example, *Lepisma saccharina.* From the order of the Collembola, for example, *Onychiurus armaus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesmaquadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphumavenae,* Myzus spp., *Phorodon humuli, Rhopalosiphum padi,* Empoasca spp., *Euscelis bilobatus, Nephotettix cincticep, Lecanium corni, Saissetia oleae, Laodelphax striatellus, Nilaparvata lugens, Aonidiella aurantii, Aspidiotus hederae,* Pseudococcus spp. Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria app. *Bucculatrix thurberiella, Phyllocnistis citrella,* Agrotis spp., Euxoa spp., Feltia spp., *Earias insulana,* Heliothis spp., *Spodoptera exigua, Mamesra brassicae, Panolis flammea, Prodenia litura,* Spodoptera spp., Trichoplusia ni, *Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varive stis,* Atomaria spp., *Oryzaephilus surinamensis,* Antho nomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Cono derus spp., *Melolontha melolontha, Amphimallon solsti tialis* and *Costelytra zealandica.* From the order of the Hymenoptera, for example, Diprion spp., Hoplocampa spp., Lasius spp., *Monomorium pharaonis* and vespa spp. From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

When used as fungicides, the active compounds according to the invention can exist in the formulations as mixtures with other known active compounds such as fungicides, insecticides, acaricides and herbicides, and as mixtures with fertilizers and growth regulators.

The active compounds can be used as such or in the form of their formulations or the use forms prepared therefrom by further dilution, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

When used as insecticides, the active compounds according to the invention can be present in their commercially available formulations and in the use forms prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, and others.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

PREPARATION EXAMPLES

Example 1

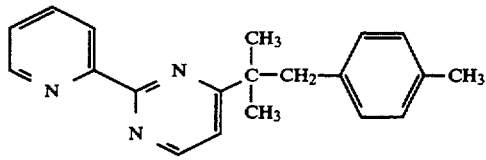

6.3 g (0.04 mol) of 2-pyridylamidine hydrochloride, 9.8 g (0.04 mol) of 1-dimethylamino-4,4-dimethyl-5-(4-methylphenyl)-pent-1-en-3-one and 10.7 g (0.05 mol) of sodium methylate are refluxed for 2 hours in 75 ml of dry methanol. After cooling to room temperature, the mixture is acidified using glacial acetic acid and subsequently concentrated in vacuo, the residue is stirred with water, the aqueous solution is decanted off, the residue is stirred with ligroin and filtered, the filtrate is concentrated in vacuo, and the residue is purified by chromatography (silica gel; eluent: ethyl acetate).

8.0 g (66% of theory) of 2-(2-pyridyl)-4-[1,1-dimethyl-2-(4-methylphenyl)-ethyl]-pyrimidine are obtained as a highly viscous oil.

$^1$H NMR (CDCl$_3$/tetramethylsilane): $\delta = 8.8$ (d, 1H, J = 6 Hz) ppm.

The following substituted pyridylpyrimidines of the general formula (I) are obtained analogously and following the general preparation instructions:

(I)

| Example No. | A | Ar | Physical properties |
|---|---|---|---|
| 2 | −C(CH$_3$)$_2$− | phenyl | $^1$H NMR*): 8.8(d, 1H, J=6Hz) |
| 3 | −C(CH$_3$)$_2$−CH$_2$− | 2,3-dichlorophenyl | $^1$H NMR*): 8.85(d, 1H, J=6Hz) |
| 4 | −C(CH$_3$)$_2$−CH$_2$−O− | 4-bromophenyl | $^1$H NMR*): 8.9(d, 1H, J=6Hz) |
| 5 | −C(CH$_3$)$_2$−CH$_2$− | 3-chlorophenyl | $^1$H NMR*): 8.8(d, 1H, J=6Hz) |
| 6 | −C(CH$_3$)$_2$−CH$_2$−O− | 3-trifluoromethylphenyl | $^1$H NMR*): 8.9(d, 1H, J=6Hz) |
| 7 | −C(CH$_3$)$_2$−CH$_2$−O− | 4-trifluoromethylphenyl | $^1$H NMR*): 8.85(d, 1H, J=6Hz) |
| 8 | −C(CH$_3$)$_2$−CH$_2$−O− | 4-fluorophenyl | $^1$H NMR*): 8.9(d, 1H, J=6Hz) |
| 9 | −C(CH$_3$)$_2$−CH$_2$−O− | 2-trifluoromethylphenyl | $^1$H NMR*): 8.8(d, 1H, J=6Hz) |

-continued (I)

| Example No. | A | Ar | Physical properties |
|---|---|---|---|
| 10 | -C(CH$_3$)$_2$-CH$_2$-O- | 3-Cl-C$_6$H$_4$- | $^1$H NMR*): 8.85(d, 1H, J=6Hz) |
| 11 | -C(CH$_3$)$_2$-CH$_2$-O- | 4-CH$_3$-C$_6$H$_4$- | m.p.: 91–93° C. |
| 12 | -C(CH$_3$)$_2$-CH$_2$- | 4-Cl-C$_6$H$_4$- | $^1$H NMR*): 8.8(d, 1H, J=6Hz) |
| 13 | -C(CH$_3$)$_2$-CH$_2$- | 3-Cl-C$_6$H$_4$- | $^1$H NMR*): 8.9(d, 1H, J=6Hz) |
| 14 | -C(CH$_3$)$_2$-CH$_2$- | 4-F-C$_6$H$_4$- | $^1$H NMR*): 8.9(d, 1H, J=6Hz) |
| 15 | -C(CH$_3$)$_2$-CH$_2$- | C$_6$H$_5$- | $^1$H NMR*): 8.8(d, 1H, J=6Hz) |
| 16 | -C(CH$_3$)$_2$-CH$_2$- | 2-F-C$_6$H$_4$- | $^1$H NMR*): 8.85(d, 1H, J=6Hz) |
| 17 | -C(CH$_3$)$_2$-CH$_2$- | 2-CH$_3$-C$_6$H$_4$- | $^1$H NMR*): 8.8(d, 1H, J=6Hz) |
| 18 | -C(CH$_3$)$_2$-CH$_2$- | 3-CH$_3$-C$_6$H$_4$- | $^1$H NMR*): 8.8(d, 1H, J=6Hz) |
| 19 | -C(CH$_3$)$_2$-CH$_2$- | 2,4-Cl$_2$-C$_6$H$_3$- | $^1$H NMR*): 8.85(d, 1H, J=6Hz) |
| 20 | -C(CH$_3$)$_2$-CH$_2$- | 4-CF$_3$-C$_6$H$_4$- | $^1$H-NMR*): δ=8.85(d, 1H; J=6Hz) |

-continued (I)

| Example No. | A | Ar | Physical properties |
|---|---|---|---|
| 21 | −C(CH₃)₂−CH₂− | −C₆H₄−CF₃ (para) | ¹H-NMR*): δ=8.8(d), 1H; J=6Hz |
| 22 | −C(CH₃)₂−CH₂−S− | phenyl | m.p.: 75–77° C. |
| 23 | −C(CH₃)₂−CH₂− | 2-CF₃-phenyl | ¹H-NMR*): δ=8.9(d), 1H; J=6Hz |
| 24 | −C(CH₃)₂−CH₂− | 3-OCH₃-phenyl | ¹H-NMR*): δ=8.85(d), 1H; J=6Hz |
| 25 | −C(CH₃)₂−CH₂−S− | 4-Cl-phenyl | ¹H-NMR*): δ=8.9(d), 1H; J=6Hz |
| 26 | −C(CH₃)₂−CH₂−O− | 2-Cl-phenyl | ¹H-NMR*): δ=8.9(d), 1H; J=6Hz |
| 27 | −C(CH₃)₂−CH₂−O− | 2,5-Cl₂-phenyl | ¹H-NMR*): δ=8.9(d), 1H; J=6Hz |
| 28 | −C(CH₃)₂−CH₂−O− | 3,4-Cl₂-phenyl | ¹H-NMR*): δ=8.9(d), 1H; J=6Hz |
| 29 | −C(CH₃)₂−CH₂− | 1-naphthyl | m.p.: 91–94° C. |
| 30 | −C(CH₃)₂−CH₂−O− | 4-Cl-phenyl | ¹H-NMR*): δ=9.0(d), 1H; J=6Hz |
| 31 | −C(CH₃)₂−CH₂−O− | 2-CH₃-4-Cl-phenyl | ¹H-NMR*): δ=8.95(d), 1H; J=6Hz |

-continued (I)

| Example No. | A | Ar | Physical properties |
|---|---|---|---|
| 32 | -C(CH₃)₂-CH₂-O- | phenyl | ¹H-NMR*): δ=8.95(d, 1H; J=6Hz) |
| 33 | -C(CH₃)₂-CH₂- | 4-OCH₃-phenyl | ¹H-NMR*): δ=8.9(d, 1H; J=6Hz) |
| 34 | -C(CH₃)₂-CH₂-O- | 2,4-dichlorophenyl | ¹H-NMR*): δ=8.9(d, 1H; J=6Hz) |
| 35 | -C(CH₃)₂-CH₂-O- | 2,3-dichlorophenyl | ¹H-NMR*): δ=8.9(d, 1H; J=6Hz) |
| 36 | -C(CH₃)₂-CH₂-O- | 4-biphenyl | ¹H-NMR*): δ=8.9(d, 1H; J=6Hz) |
| 37 | -C(CH₃)₂-CH₂-O- | 3,4-dichlorophenyl | ¹H-NMR*): δ=8.95(d, 1H; J=6Hz) |
| 38 | -C(CH₃)₂-CH₂-O- | 2,3-dichlorophenyl | ¹H-NMR*): δ=8.95(d, 1H; J=6Hz) |
| 39 | -C(CH₃)₂-CH₂- | naphthyl | ¹H-NMR*): δ=8.8(d, 1H; J=6Hz) |
| 40 | -C(CH₃)₂-CH₂-O- | 2,4,5-trichlorophenyl | ¹H-NMR*): δ=8.9(d, 1H; J=6Hz) |
| 41 | -C(CH₃)₂-CH₂-S- | 4-CF₃-phenyl | ¹H-NMR*): δ=8.9(d, 1H; J=6Hz) |

*)The ¹H NMR spectra were recorded in deuterochloroform (CDCl₃) or hexadeuterodimethylsulfoxid (DMSO-d₆) with tetramethylsilane (TMS) as the internal standard. The figures indicate the chemical shift as value in ppm.

Example III-1

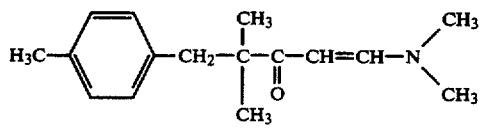

33.3 g (0.175 mol) of 4-(4-methylphenyl)-3,3-dimethylbutan-2-one and 22.9 g (0.193 mol) of dimethylformamide dimethyl acetal are combined and the mixture is refluxed for 2 hours. After cooling to room temperature, the mixture is concentrated in vacuo, and the residue is stirred with ligroin, filtered off with suction and dried.

14.7 g (34% of theory) of 1-dimethylamino-4,4-dimethyl-(5-(4-methylphenyl)-pent-1-en-3-one of melting point 74° to 76° C. are obtained.

Preparation of the starting compound:

Example IV-1

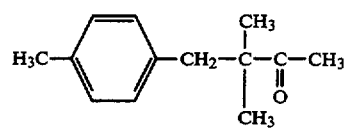

To 84 g (1.5 mol) of powdered potassium hydroxide and 4.8 g (0.015 mol) of tetrabutylammoniumbromide in 125 ml of dry toluene there are added dropwise with stirring at room temperature first 51.6 g (0.6 mol) of methyl isopropyl ketone and subsequently 70.3 g (0.5 ml) of 4-methylbenzyl chloride in 125 ml of dry toluene, and the mixture is then stirred at room temperature for 16 hours. For working up, the reaction mixture is treated with water, the organic phase is separated off, dried over sodium sulphate and concentrated, and the concentrate is distilled in vacuo.

36.1 g (38% of theory) of 3,3-dimethyl-4-(4-methylphenyl)-butan-2-one are obtained, boiling point 98° to 101° C. at 5 mbar.

The following enamines of the general formula (III) are obtained analogously and following the general preparation instructions:

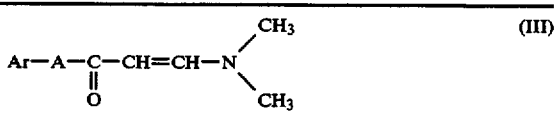

(III)

| Example No. | Ar | A | Physical properties |
|---|---|---|---|
| III-2 | CF$_3$—⟨phenyl⟩— | —O—CH$_2$—C(CH$_3$)(CH$_3$)— | $^1$H NMR*): 5.25(d, 1H, J=12Hz) |
| III-3 | ⟨phenyl⟩— | —C(CH$_3$)(CH$_3$)— | m.p.: 63–66° C. |
| III-4 | Cl,Cl—⟨phenyl⟩— | —CH$_2$—C(CH$_3$)(CH$_3$)— | $^1$H NMR*): 5.25(d, 1H, J=12Hz) |
| III-5 | Cl—⟨phenyl⟩— (ortho) | —CH$_2$—C(CH$_3$)(CH$_3$)— | $^1$H NMR*): 5.25(d, 1H, J=12Hz) |
| III-6 | Br—⟨phenyl⟩— | —O—CH$_2$—C(CH$_3$)(CH$_3$)— | $^1$H NMR*): 5.3(d, 1H, J=12Hz) |
| III-7 | F$_3$C—⟨phenyl⟩— | —O—CH$_2$—C(CH$_3$)(CH$_3$)— | $^1$H NMR*): 5.25(d, 1H, J=12Hz) |

-continued $$Ar-A-\underset{O}{\underset{\|}{C}}-CH=CH-N\begin{matrix}CH_3\\ \\CH_3\end{matrix} \quad (III)$$

| Example No. | Ar | A | Physical properties |
|---|---|---|---|
| III-8 | 2-CF$_3$-C$_6$H$_4$- | —O—CH$_2$—C(CH$_3$)$_2$— | $^1$H NMR*): 5.3(d, 1H, J=12Hz) |
| III-9 | 4-F-C$_6$H$_4$- | —O—CH$_2$—C(CH$_3$)$_2$— | $^1$H NMR*): 5.25(d, 1H, J=12Hz) |
| III-10 | 3-Cl-C$_6$H$_4$- | —O—CH$_2$—C(CH$_3$)$_2$— | $^1$H NMR*): 5.25(d, 1H, J=12Hz) |
| III-11 | 4-CH$_3$-C$_6$H$_4$- | —O—CH$_2$—C(CH$_3$)$_2$— | $^1$H NMR*): 5.25(d, 1H, J=12Hz) |
| III-12 | 3-Cl-C$_6$H$_4$- | —CH$_2$—C(CH$_3$)$_2$— | m.p.: 99–101° C. |
| III-13 | 4-F-C$_6$H$_4$- | —CH$_2$—C(CH$_3$)$_2$— | m.p.: 79–81° C. |
| III-14 | C$_6$H$_5$- | —CH$_2$—C(CH$_3$)$_2$— | m.p.: 54–56° C. |
| III-15 | 2-F-C$_6$H$_4$- | —CH$_2$—C(CH$_3$)$_2$— | $^1$H NMR*): 5.25(d, 1H, J=12Hz) |
| III-16 | 2-CH$_3$-C$_6$H$_4$- | —CH$_2$—C(CH$_3$)$_2$— | $^1$H NMR*): 5.2(d, 1H, J=12Hz) |
| III-17 | 3-CH$_3$-C$_6$H$_4$- | —CH$_2$—C(CH$_3$)$_2$— | $^1$H NMR*): 5.2(d, 1H, J=12Hz) |
| III-18 | 2,4-Cl$_2$-C$_6$H$_3$- | —CH$_2$—C(CH$_3$)$_2$— | $^1$H NMR*): 5.2(d, 1H, J=12Hz) |

-continued $$Ar-A-\underset{\underset{O}{\|}}{C}-CH=CH-N\underset{CH_3}{\overset{CH_3}{\diagup}} \quad (III)$$

| Example No. | Ar | A | Physical properties |
|---|---|---|---|
| III-19 | 4-Cl-C₆H₄- | -CH₂-C(CH₃)₂- | ¹H NMR*): 5.2(d, 1H, J=12Hz) |
| III-20 | 3-CF₃-C₆H₄- | -CH₂-C(CH₃)₂- | ¹H-NMR*): δ=5.2(d, 1H; J=12Hz) |
| III-21 | C₆H₅- | -S-CH₂-C(CH₃)₂- | ¹H-NMR*): δ=5.2(d, 1H; J=12Hz) |
| III-22 | 2-CF₃-C₆H₄- | -CH₂-C(CH₃)₂- | ¹H-NMR*): δ=5.3(d, 1H; J=12Hz) |
| III-23 | 4-CF₃-C₆H₄- | -CH₂-C(CH₃)₂- | m.p.: 121-123° C. |
| III-24 | 3-CH₃O-C₆H₄- | -CH₂-C(CH₃)₂- | ¹H-NMR*): δ=5.25(d, 1H; J=12Hz) |
| III-25 | 4-Cl-C₆H₄- | -S-CH₂-C(CH₃)₂- | ¹H-NMR*): δ=5.2(d, 1H; J=12Hz) |
| III-26 | 2-Cl-C₆H₄- | -O-CH₂-C(CH₃)₂- | ¹H-NMR*): δ=5.35(d, 1H; J=12Hz) |
| III-27 | 2,4-Cl₂-C₆H₃- | -O-CH₂-C(CH₃)₂- | m.p.: 99-102° C. |
| III-28 | 4-Cl-3-CH₃-C₆H₃- | -O-CH₂-C(CH₃)₂- | ¹H-NMR*): δ=5.25(d, 1H; J=12Hz) |

-continued $$Ar-A-\underset{\underset{O}{\|}}{C}-CH=CH-N\underset{CH_3}{\overset{CH_3}{<}} \quad (III)$$

| Example No. | Ar | A | Physical properties |
|---|---|---|---|
| III-29 | 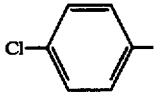 | —O—CH$_2$—C(CH$_3$)$_2$— | $^1$H-NMR*): δ=5.25(d, 1H; J=12Hz) |
| III-30 | 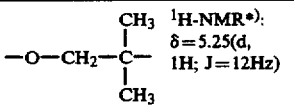 | —O—CH$_2$—C(CH$_3$)$_2$— | $^1$H-NMR*): δ=5.2(d, 1H; J=12Hz) |
| III-31 | 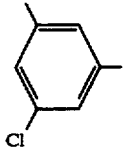 | —O—CH$_2$—C(CH$_3$)$_2$— | $^1$H-NMR*): δ=5.3(d, 1H; J=12Hz) |
| III-32 | 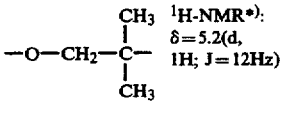 | —CH$_2$—C(CH$_3$)$_2$— | $^1$H-NMR*): δ=5.15(d, 1H; J=12Hz) |
| III-33 |  | —O—CH$_2$—C(CH$_3$)$_2$— | $^1$H-NMR*): δ=5.2(d, 1H; J=12Hz) |
| III-34 | 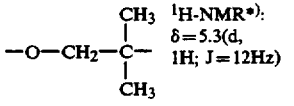 | —O—CH$_2$—C(CH$_3$)$_2$— | m.p.: 71–74° C. |
| III-35 | 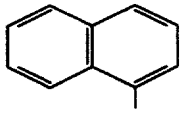 | —O—CH$_2$—C(CH$_3$)$_2$— | $^1$H-NMR*): δ=5.35(d, 1H; J=12Hz) |
| III-36 | 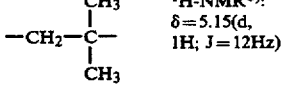 | —O—CH$_2$—C(CH$_3$)$_2$— | $^1$H-NMR*): δ=5.3(d, 1H; J=12Hz) |
| III-37 | 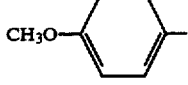 | —O—CH$_2$—C(CH$_3$)$_2$— | $^1$H-NMR*): δ=5.2(d, 1H; J=12Hz) |
| III-38 | 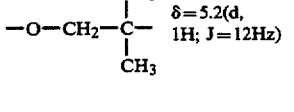 | —O—CH$_2$—C(CH$_3$)$_2$— | $^1$H-NMR*): δ=5.3(d, 1H; J=12Hz) |

-continued $$Ar-A-\underset{\underset{O}{\|}}{C}-CH=CH-N\underset{CH_3}{\overset{CH_3}{\diagup}} \qquad (III)$$

| Example No. | Ar | A | Physical properties |
|---|---|---|---|
| III-39 | 2-naphthyl | $-CH_2-\underset{CH_3}{\overset{CH_3}{\underset{|}{\overset{|}{C}}}}-$ | $^1$H-NMR*): $\delta = 5.2$(d, 1H; J = 12Hz) |
| III-40 | 2,4,5-trichlorophenyl | $-O-CH_2-\underset{CH_3}{\overset{CH_3}{\underset{|}{\overset{|}{C}}}}-$ | $^1$H-NMR*): $\delta = 5.32$(d, 1H; J = 12Hz) |
| III-41 | 4-(F$_3$C)phenyl | $-S-CH_2-\underset{CH_3}{\overset{CH_3}{\underset{|}{\overset{|}{C}}}}-$ | $^1$H-NMR*): $\delta = 5.2$(d, 1H; J = 12Hz) |
| III-42 | 3-chlorophenyl | $-S-CH_2-\underset{CH_3}{\overset{CH_3}{\underset{|}{\overset{|}{C}}}}-$ | $^1$H-NMR*): $\delta = 5.2$(d, 1H; J = 12Hz) |
| III-43 | 4-methoxyphenyl | $-S-CH_2-\underset{CH_3}{\overset{CH_3}{\underset{|}{\overset{|}{C}}}}-$ | $^1$H-NMR*): $\delta = 5.2$(d, 1H; J = 12Hz) |
| III-44 | 4-fluorophenyl | $-S-CH_2-\underset{CH_3}{\overset{CH_3}{\underset{|}{\overset{|}{C}}}}-$ | $^1$H-NMR*): $\delta = 5.2$(d, 1H; J = 12Hz) |
| III-45 | 2-chlorophenyl | $-S-CH_2-\underset{CH_3}{\overset{CH_3}{\underset{|}{\overset{|}{C}}}}-$ | $^1$H-NMR*): $\delta = 5.2$(d, 1H; J = 12Hz) |

*)The $^1$H NMR spectra were recorded in deuterochloroform (CDCl$_3$) with tetramethylsilane (TMS) as the internal standard. The figures indicate the chemical shift as δ value in ppm.

Use Examples

In the Use Examples which follow, the compounds listed below were applied as comparison substances:

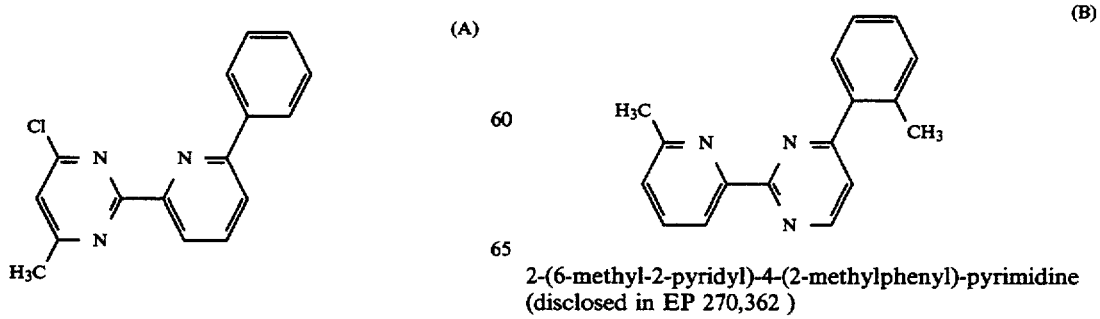

(A) 2-(6-phenyl-2-pyridyl)-4-chloro-6-methyl-pyrimidine (disclosed in EP 259,139)

(B) 2-(6-methyl-2-pyridyl)-4-(2-methylphenyl)-pyrimidine (disclosed in EP 270,362)

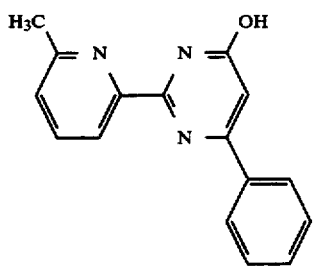

2-(6-methyl-2-pyridyl)-4-hydroxy-6-phenyl-pyrimidine (disclosed in EP 270,362)

Example A

*Cochliobolus sativus* test (barley)/protective

Solvent: 100 parts by weight of dimethylformamide Emulsifier: 0.25 parts by weight of alkylaryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Cochliobolus sativus*. The plants remain in an incubation cabinet for 48 hours at 20° C. and 100% relative atmospheric humidity.

The plants are placed in a greenhouse at a temperature of approx. 20° C. and a relative atmospheric humidity of approx. 80%.

The test is evaluated 7 days after inoculation.

The compounds of the Preparation Examples 5, 6, 8, 9, 10 and 11 show a degree of activity of 81–100% at an active compound concentration of 250ppm. The comparison examples (A), (B) and (C) show at the same active compound concentration no activity.

Example B

Erysiphe test (wheat)/protective

Solvent: 100 parts by weight of dimethylformamide Emulsifier: 0.25 parts by weight of alkylaryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. *tritici.*

The plants are placed in a greenhouse at a temperature of approx. 20° C. and a relative atmospheric humidity of approx. 80% to favour the development of mildew pustules.

The test is evaluated 7 days after inoculation.

The compounds of the Preparatton Examples 2 and 7 show a degree of activity of 100% at an active compound concentration of 250 ppm. The comparison example (B) shows no activity.

Example C

Uncinula test (grapevine)/protective

Solvent: 4.7 parts by weight of acetone Emulsifier: 0.3 parts by weight of alkyl-aryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Uncinula necator.*

The plants are subsequently placed in a greenhouse at 23° to 24° C. and a relative atmospheric humidity of approx. 75%.

The test is evaluated 14 days after inoculaton

The compounds of the Preparation Examples 1, 4, 5, 7, 8, 9, 10, 12, 13, 14, 15, 16, 17, 18 and 19 show a degree of activity of 82°–100% at an active compound concentration of 10 ppm. The comparison example (A) shows a degree of activity of 69% at the same active compound concentration.

Example D

Plutella test

Solvent: 7 parts by weight of dimethylformamide Emulsifier: 1 part by weight of alkylaryl polyglycol ether To prepare a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by dipping into the preparation of active compound of the desired concentration and are infected with caterpillars of the cabbage moth (*Plutella maculipennis*) while the leaves are moist.

After the specified time, the destruction is determined in %. 100% denotes that all caterpillars have been killed; 0% denotes that no caterpillars have been killed.

In this test, for example, the compound (2) of the Preparation Examples shows a degree of mortality of 100% at an active compound concentration of 0.1%.

Example E

Nephotettix text

Solvent: 7 parts by weight of dimethylformamide Emulsifier: 1 part by weight of alkylaryl polyglycol ether To prepare a suitable preparation of active compound, 1 part by weight of active compound is mixed with the stated amount of solvent and the stated amount of emulsifier, and the concentrate is diluted with water to the desired concentration.

Rice seedlings (*Oryza satira*) are treated by dipping into the active compound preparation of the desired concentration and are infested with larvae of the green rice cicada (*Nephotettix cincticeps*) while the seedlings are moist.

After the specified time, the destruction is determined in %. 100% denotes that all cicadas have been killed; 0% denotes that no cicadas have been killed.

We claim:

1. A pyridylpyrimidine compound of the formula

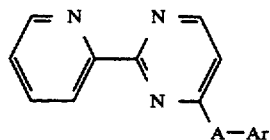

in which

A represents a radical of the formula

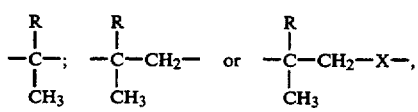

where

R represents straight-chain or branched alkyl having 1 to 4 carbon atoms,

X represents oxygen or sulphur and

Ar represents phenyl which is optionally monosubstituted to pentasubstituted by identical or different substituents, wherein the substituents are halogen, cyano, nitro, straight-chain or branched alkyl, straight-chain or branched alkoxy or straight-chain or branched alkylthio, each having 1 to 4 carbon atoms in the alkyl moieties, straight-chain or branched halogenoalkyl, straight-chain or branched halogenoalkoxy or straight-chain or branched halogenoalkylthio, each having 1 to 4 carbon atoms in the alkyl moiety and 1 to 9 identical or different halogen atoms, straight-chain or branched alkoxycarbonyl or alkoxyiminoalkyl, each having 1 to 4 carbon atoms in the individual alkyl moieties, or phenyl which is optionally monosubstituted to pentasubstituted by identical or different substituents from the series group consisting of halogen and straight-chain or branched alkyl having 1 to 4 carbon atoms.

2. A pyridylpyrimidine compound according to claim 1, in which

A represents a radical of the formula

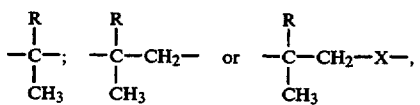

where

R in each case represents methyl or ethyl,

X represents oxygen or sulphur and

Ar represents phenyl which is optionally monosubstituted to trisubstituted by identical or different substituents, wherein the substituents are fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, trifluoromethylthio, methoxycarbonyl, ethoxycarbonyl, methoxyiminomethyl, ethoxyiminomethyl, methoxyiminoethyl, ethoxyiminoethyl, or phenyl which is optionally mono- substituted to trisubstituted by identical or different substituents selected from the group consisting of fluorine, chlorine, bromine, methyl and ethyl.

3. A composition for combatting fungi, arthropods, or menatodes which comprises an effective amount of a compound according to claim 1 and an inert carrier.

4. A method for combatting fungi, arthropods or menatodes which comprises applying thereto an effective amount of a compound of claim 1.

5. A process for the preparation of a pyridylpyrimidine compound of the formula

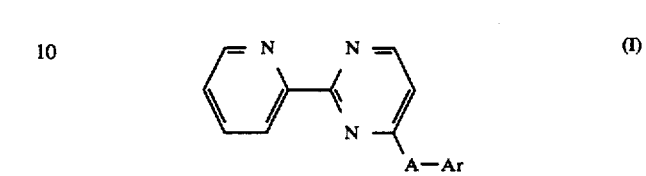

in which

A represents a radical of the formula

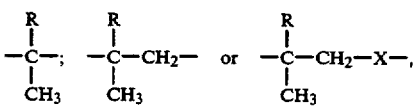

where

R represents straight-chain or branched alkyl having 1 to 4 carbon atoms,

X represents oxygen or sulphur and

Ar represents phenyl which is optionally monosubstituted to pentasubstituted by identical or different substituents, wherein the substituents are halogen, cyano, nitro, straight-chain or branched alkyl, straight-chain or branched alkoxy or straight-chain or branched alkylthio, each having 1 to 4 carbon atoms in the alkyl moieties, straight-chain or branched halogenoalkyl, straight-chain or branched halogenoalkoxy or straight-chain or branched halogenoalkylthio, each having 1 to 4 carbon atoms in the alkyl moiety and 1 to 9 identical or different halogen atoms, straight-chain or branched alkoxycarbonyl or alkoxyiminoalkyl, each having 1 to 4 carbon atoms in the individual alkyl moieties, or phenyl which is optionally monosubstituted to pentasubstituted by identical or different substituents from the series group consisting of halogen and straight-chain or branched alkyl having 1 to 4 carbon atoms, characterised in that 2-pyridylamidine salts of the formula (II)

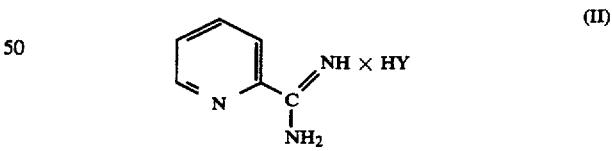

in which

Y represents the anion of an inorganic mineral acid, are reacted with examines of the formula (III)

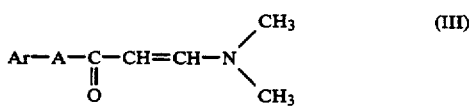

in which

Ar and A have the abovementioned meaning, if appropriate in the presence of a diluent and if appropriate in the presence of a reaction auxiliary.

* * * * *

UNITED STATES PATENT AND TRADEMARK OFFICE
CERTIFICATE OF CORRECTION

PATENT NO. : 5,416,088
DATED : May 16, 1995
INVENTOR(S) : Heinemann, et al.

It is certified that error appears in the above-indentified patent and that said Letters Patent is hereby corrected as shown below:

Col. 38, line 2   Delete " manatodes " and substitute -- nematodes --

Col. 38, line 5   Delete " menatodes " and substitute -- nematodes --

Signed and Sealed this

Twenty-fourth Day of October, 1995

Attest:

BRUCE LEHMAN

*Attesting Officer*  *Commissioner of Patents and Trademarks*